US012806437B2

(12) United States Patent
Dijkstra et al.

(10) Patent No.: US 12,806,437 B2
(45) Date of Patent: Nov. 24, 2026

(54) STAND FOR THERAPY PADS

(71) Applicant: LUMAFLEX LLC, Minneapolis, MN (US)

(72) Inventors: Alain Dijkstra, Amstelveen (NL); John Graham Harper, Minneapolis, MN (US); Liu Si Yuan, Minneapolis, MN (US); Ye Qi, Shenzhen (CN); Chen Shoufeng, Shenzhen (CN)

(73) Assignee: LUMAFLEX LLC

( * ) Notice: Subject to any disclaimer, the term of this patent is extended or adjusted under 35 U.S.C. 154(b) by 213 days.

(21) Appl. No.: 18/641,516

(22) Filed: Apr. 22, 2024

(65) Prior Publication Data

US 2025/0325828 A1 Oct. 23, 2025

(51) Int. Cl.
*A61N 5/06* (2006.01)

(52) U.S. Cl.
CPC ........ *A61N 5/06* (2013.01); *A61N 2005/0633* (2013.01); *A61N 2005/0634* (2013.01)

(58) Field of Classification Search
CPC .............. A61N 5/06; A61N 2005/0633; A61N 2005/0634
See application file for complete search history.

(56) References Cited

U.S. PATENT DOCUMENTS

| | | | | |
|---|---|---|---|---|
| 4,651,263 A * | 3/1987 | Hancock | F16M 11/24 | 607/91 |
| 4,740,707 A * | 4/1988 | Thaw | A61N 5/0614 | 607/94 |
| 9,924,005 B1 * | 3/2018 | McElderry | H04M 1/04 | |
| 10,663,124 B1 * | 5/2020 | Smith | F21S 2/005 | |
| 10,828,505 B2 | 11/2020 | Nelson et al. | | |
| 11,033,752 B2 | 6/2021 | Strahan et al. | | |
| 11,988,368 B1 * | 5/2024 | Harnisch | F21V 21/30 | |
| 2006/0020308 A1 * | 1/2006 | Muldner | A61N 5/0616 | 607/90 |
| 2006/0229689 A1 * | 10/2006 | Ferguson | A61N 5/0616 | 607/91 |
| 2007/0038269 A1 * | 2/2007 | Whitehurst | A61N 5/0616 | 607/88 |
| 2016/0361563 A1 * | 12/2016 | Wang | H05K 5/0086 | |
| 2018/0266666 A1 * | 9/2018 | Liao | F21L 14/04 | |
| 2022/0016435 A1 * | 1/2022 | Pfiffner | A61N 5/0616 | |
| 2023/0001227 A1 * | 1/2023 | Boyajian | A61N 5/062 | |
| 2023/0145771 A1 * | 5/2023 | Boyajian | A61K 41/0061 | 424/9.1 |

(Continued)

*Primary Examiner* — Nathan J Jenness
(74) *Attorney, Agent, or Firm* — Willie Jacques; Emanus LLC

(57) ABSTRACT

Embodiments of the present invention provide a stand for therapy pads. The stand includes a control module including a plurality of docking stations configured to dock therewithin a plurality of respective energy storage units, the plurality of energy storage units configured to store electrical energy. Furthermore, the stand includes a frame mechanically coupled to the control module, the frame configured to fasten thereupon one or more therapy pads. Furthermore, the control module is configured to supply electrical power to the one or more therapy pads through one or more power supply terminals included within the frame, the one or more power supply terminals configured to contact one or more complementary power-receiving terminals of the one or more respective therapy pads.

22 Claims, 13 Drawing Sheets

(56) References Cited

U.S. PATENT DOCUMENTS

| | | | | |
|---|---|---|---|---|
| 2024/0077181 | A1* | 3/2024 | Dee | F21V 33/0084 |
| 2025/0180193 | A1* | 6/2025 | Dee | F21V 21/34 |
| 2025/0271125 | A1* | 8/2025 | Mutchler | F21V 21/24 |

* cited by examiner

STAND FOR THERAPY PADS

TECHNICAL FIELD

The present invention relates generally to devices used in the application of therapy on external surfaces of the body of a user. More specifically, the present invention relates to auxiliary apparatuses used for mounting and operating the devices used in the application of the therapy.

BACKGROUND ART

Devices of various types for both therapeutic and recreational needs have been well-established in the field for a considerable period. Conventional therapeutic devices include various stimulation elements like irradiation sources, electrodes, ultrasonic wave generators, vibratory elements, heating elements, cooling elements, and combinations thereof for providing therapy sessions to an individual for skin rejuvenation, muscle relaxation, pain relief, and other therapeutic benefits. Exposure to irradiation sources in collaboration with other stimulation elements such as the heating elements, the electrodes, and the like is believed to induce a chemical change in the brain, alleviating mood and mitigating symptoms associated with specific conditions.

However, such devices are generally designed for handheld use and are of small size for ease of use and portability. Handheld devices cover a smaller area and therefore it can take longer to treat a wider area of the body. Moreover, due to the smaller treatment area, sessions with handheld devices may take longer than expected. Furthermore, holding a handheld device requires a steady hand. Inconsistent application can lead to uneven treatment results. Not all handheld therapy devices are created equal. Some may lack sufficient power output, have uneven therapy distribution, or not operate optimally for therapeutic effects. In addition, while generally less expensive than large panels, high-quality handheld devices can still be a significant investment.

Therefore, there is a need in the art for a stand for therapy pads that allow larger panels to be installed thereupon for providing comprehensive therapy over larger surface areas of the human body.

OBJECTS OF THE INVENTION

Some of the objects of the present invention are as follows:

An object of the present invention is to provide a stand for therapy pads that allow several therapy pads to be installed onto the stand for providing therapy covering larger surface areas of the human body simultaneously.

Another object of the present invention is to provide a stand for therapy pads that is capable of providing sufficient electrical power for the several therapy pads to be activated simultaneously.

Another object of the present invention is to provide a stand for therapy pads that allow the therapy pads to be oriented in several different orientations allowing therapy to be applied to regions of the human body that may generally be inaccessible through therapy devices currently available in the art.

Another object of the present invention is to provide a stand for therapy pads, that is simple in construction and convenient to use without needing specialized knowledge to operate the therapy pads for providing therapy to the human body.

Another object of the present invention is to provide a stand for therapy pads that can be operated to change the operational characteristics of stimulation elements such as irradiation sources, electrodes, ultrasonic wave generators, vibratory elements, heating elements, cooling elements, and combinations thereof, installed with the therapy pads by modifying the amount of electrical current being supplied to the stimulation elements.

SUMMARY OF THE INVENTION

According to a first aspect of the present invention, there is provided a stand for therapy pads. The stand includes a control module including a plurality of docking stations configured to dock therewithin a plurality of respective energy storage units, the plurality of energy storage units configured to store electrical energy. The stand also includes a frame mechanically coupled to the control module, the frame configured to fasten thereupon one or more therapy pads. Furthermore, the control module is configured to supply electrical power to the one or more therapy pads through one or more power supply terminals included within the frame, the one or more power supply terminals configured to contact one or more complementary power-receiving terminals of the one or more respective therapy pads.

In one embodiment of the invention, the one or more power supply terminals are configured to mechanically couple to the one or more respective power-receiving terminals through magnetic coupling.

In one embodiment of the invention, the frame further includes a first telescopic member includes a first proximal end and a first distal end, the first proximal end fastened to the control module, wherein a first length of the first telescopic member is adjustable, a second telescopic member including a second proximal end and a second distal end, the second proximal end pivotably coupled to the first distal end, wherein a second length of the second telescopic member is adjustable, a holding bracket pivotably coupled to the second distal end, wherein the holding bracket is configured to pivot about the second distal end, one or more first holding panels fastened to the holding bracket, the one or more first holding panels configured to fasten thereupon the one or more respective therapy pads, and one or more second holding panels pivotably coupled to the one or more first holding panels, the one or more second holding panels configured to fasten thereupon one or more respective therapy pads.

In one embodiment of the invention, each one of the one or more first holding panels and the one or more second holding panels includes a top member, a bottom member, and one or more lateral members connecting the top member and the bottom member.

In one embodiment of the invention, each one of the top member and the bottom member includes one or more engaging members configured to engage with complementary engaging members of the therapy pads.

In one embodiment of the invention, one or more respective lateral lengths of the one or more lateral members are adjustable.

In one embodiment of the invention, the first telescopic member includes a first movable arm and a first stationary arm, the first movable arm configured to translate relative to the first stationary arm, the second telescopic member includes a second movable arm and a second stationary arm, the second movable arm configured to translate relative to the second stationary arm, the frame further including an actuator arm connected between the first movable arm and the second movable arm.

In one embodiment of the invention, the stand further includes a translation lock provided between the first movable arm and the first stationary arm, the translation lock configured to arrest the translation of the first movable arm relative to the first stationary arm.

In one embodiment of the invention, the stand further includes one or more shoes configured to support the control module and the frame.

In one embodiment of the invention, each one of the one or more shoes includes a wheel for transporting the stand from one location to another location.

In one embodiment of the invention, the control module further includes a user interface configured to receive control input signals to modify operational characteristics of the one or more therapy pads.

In one embodiment of the invention, the control module further includes a communication interface configured to receive control input signals from a user computing device, over a communication network, to modify operational characteristics of the one or more therapy pads.

According to a second aspect of the present invention, there is provided a stand for therapy pads. The stand includes a control module including a plurality of docking stations configured to dock therewithin a plurality of respective energy storage units, the plurality of energy storage unit configured to store electrical energy. The stand further includes a frame mechanically coupled to the control module. The frame includes a first telescopic member including a first proximal end and a first distal end, the first proximal end fastened to the control module, wherein a first length of the first telescopic member is adjustable, a second telescopic member including a second proximal end and a second distal end, the second proximal end pivotably coupled to the first distal end, wherein a second length of the second telescopic member is adjustable, a holding bracket pivotably coupled to the second distal end, wherein the holding bracket is configured to pivot about the second distal end, one or more first holding panels fastened to the holding bracket, the one or more first holding panels configured to fasten thereupon the one or more respective therapy pads, and one or more second holding panels pivotably coupled to the one or more first holding panels, the one or more second holding panels configured to fasten thereupon one or more respective therapy pads.

In one embodiment of the invention, the first telescopic member includes a first movable arm and a first stationary arm, the first movable arm configured to translate relative to the first stationary arm, the second telescopic member includes a second movable arm and a second stationary arm, the second movable arm configured to translate relative to the second stationary arm, the frame further including an actuator arm connected between the first movable arm and the second movable arm.

In one embodiment of the invention, the control module further includes a user interface configured to receive control input signals to modify operational characteristics of the one or more therapy pads.

According to a third aspect of the present invention, there is provided a method of using a stand for therapy pads. The method includes providing the stand. The stand includes a control module including a plurality of docking stations configured to dock therewithin a plurality of respective energy storage units, the plurality of energy storage units configured to store electrical energy, and a frame mechanically coupled to the control module, the frame configured to fasten thereupon one or more therapy pads, wherein the control module is configured to supply electrical power to the one or more therapy pads through one or more power supply terminals included within the frame, the one or more power supply terminals configured to contact one or more complementary power-receiving terminals of the one or more respective therapy pads, and wherein the control module further includes a user interface configured to receive control input signals to modify operational characteristics of the one or more therapy pads. The method further includes fastening the one or more therapy pads to the frame, as a result wherein, the one or more complementary power-receiving terminals of the one or more respective therapy pads make contact with the one or more respective power supply terminals of the frame. The method also includes providing control input signals through the user interface to modify the operational characteristics of the one or more therapy pads.

In one embodiment of the invention, the method further includes receiving the control input signals from a user computing device, over a communication network, to modify the operational characteristics of the one or more therapy pads.

In one embodiment of the invention, the frame further includes a first telescopic member including a first proximal end and a first distal end, the first proximal end fastened to the control module, wherein a first length of the first telescopic member is adjustable, a second telescopic member including a second proximal end and a second distal end, the second proximal end pivotably coupled to the first distal end, wherein a second length of the second telescopic member is adjustable, wherein the first telescopic member comprises a first movable arm and a first stationary arm, the first movable arm configured to translate relative to the first stationary arm, the second telescopic member comprises a second movable arm and a second stationary arm, the second movable arm configured to translate relative to the second stationary arm, the frame further including an actuator arm connected between the first movable arm and the second movable arm, a holding bracket pivotably coupled to the second distal end, wherein the holding bracket is configured to pivot about the second distal end, one or more first holding panels fastened to the holding bracket, the one or more first holding panels configured to fasten thereupon the one or more respective therapy pads. The method further includes adjusting the first and the second lengths of the first and the second telescopic members respectively.

In one embodiment of the invention, the adjusting of the first and the second lengths of the first and the second telescopic members respectively is performed through the control module.

In one embodiment of the invention, the stand further includes a translation lock provided between the first movable arm and the first stationary arm, the translation lock configured to arrest the translation of the first movable arm relative to the first stationary arm, and the method further includes arresting the translation of the first movable arm relative to the first stationary arm by engaging the translation lock.

In one embodiment of the invention, the arresting of the translation of the first movable arm relative to the first stationary arm by engaging the translation lock is performed through the control module.

In one embodiment of the invention, the stand further includes one or more shoes configured to support the control module and the frame wherein each one of the one or more shoes includes a wheel for transporting the stand from one location to another location, and the method further includes transporting the stand from one location to another location.

In the context of the specification, the term "processor" refers to one or more of a microprocessor, a microcontroller, a general-purpose processor, a Field Programmable Gate Array (FPGA), a Neural Processing Unit (NPU), a Graphics Processing Unit (GPU), a Tensor Processing Unit (TPU), an Application Specific Integrated Circuit (ASIC), and the like.

In the context of the specification, the phrase "memory unit" refers to volatile storage memory, such as Static Random Access Memory (SRAM) and Dynamic Random Access Memory (DRAM) of types such as Asynchronous DRAM, Synchronous DRAM, Double Data Rate SDRAM, Rambus DRAM, and Cache DRAM, etc.

In the context of the specification, the phrase "storage device" refers to a non-volatile storage memory such as EPROM, EEPROM, flash memory, or the like.

In the context of the specification, the phrase "communication interface" refers to a device or a module enabling direct connectivity via wires and connectors such as USB, HDMI, VGA, or wireless connectivity such as Bluetooth or Wi-Fi, or Local Area Network (LAN) or Wide Area Network (WAN) implemented through TCP/IP, IEEE 802.x, GSM, CDMA, LTE, or other equivalent protocols.

In the context of the specification, the phrase "communication network" refers to a group of several connected devices including computing devices (such as desktops, mobile handheld devices, tablet PCs, notebooks, etc.), local and remotely located servers (such as web servers, application servers, database servers, Application Program Interface (API) servers, load balancers, compute nodes, and the like), routers, antennas, modems, multiplexers, demultiplexers, and the like. In that regard, the aforementioned connected devices may be able to exchange data signals through wired and/or wireless means as per several combinations of several different communication protocols such as 802.11 (Wi-Fi), 802.3 (Ethernet), Bluetooth, NFC, ZigBee and 3GPP protocols such as HSPA, HSDPA, LTE, GSM, CDMA, WLL and the like.

In the context of this specification, terms like "light", "radiation", "irradiation", "emission" and "illumination", etc. refer to electromagnetic radiation in frequency ranges varying between the Ultraviolet (UV) frequencies and Infrared (IR) frequencies and wavelengths (including all visible light frequencies and wavelengths), wherein the range is inclusive of UV and IR frequencies and wavelengths. It is to be noted here that UV radiation can be categorized in several manners depending on respective wavelength ranges, all of which are envisaged to be under the scope of this invention. For example, UV radiation can be categorized as, Hydrogen Lyman-a (122-121 nm), Far UV (200-122 nm), Middle UV (300-200 nm), and Near UV (400-300 nm). The UV radiation may also be categorized as UVA (400-315 nm), UVB (315-280 nm), and UVC (280-100 nm) Similarly, IR radiation may also be categorized into several categories according to respective wavelength ranges which are again envisaged to be within the scope of this invention. A commonly used subdivision scheme for IR radiation includes Near IR (0.75-1.4 μm), Short-Wavelength IR (1.4-3 μm), Mid-Wavelength IR (3-8 μm), Long-Wavelength IR (8-15 μm) and Far IR (15-1000 μm).

In the context of the specification, the term "polymer" or "plastic" refers to a material made up of long chains of organic molecules (having eight or more organic molecules) including, but not limited to, carbon, nitrogen, oxygen, and hydrogen as their constituent elements. The term polymer is envisaged to include both naturally occurring polymers such as wool, and synthetic polymers such as polyethylene and nylon.

In the context of the specification, the phrase "diaphanous material" refers to a material that allows at least a portion of one or more forms of electromagnetic radiation (such as Infrared, Ultraviolet, X-rays, Visible Light, Microwaves, Radio Waves, etc.) to pass through them. The diaphanous materials can be transparent (allowing one or more forms of electromagnetic radiation to pass through with minimal scattering) or translucent (allowing one or more forms of electromagnetic radiation to pass through with appreciable diffusion or scattering). Diaphanous materials can be dense, like glass, or have an open structure, like wire mesh or a woven fabric.

BRIEF DESCRIPTION OF THE ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

Figure 3A:
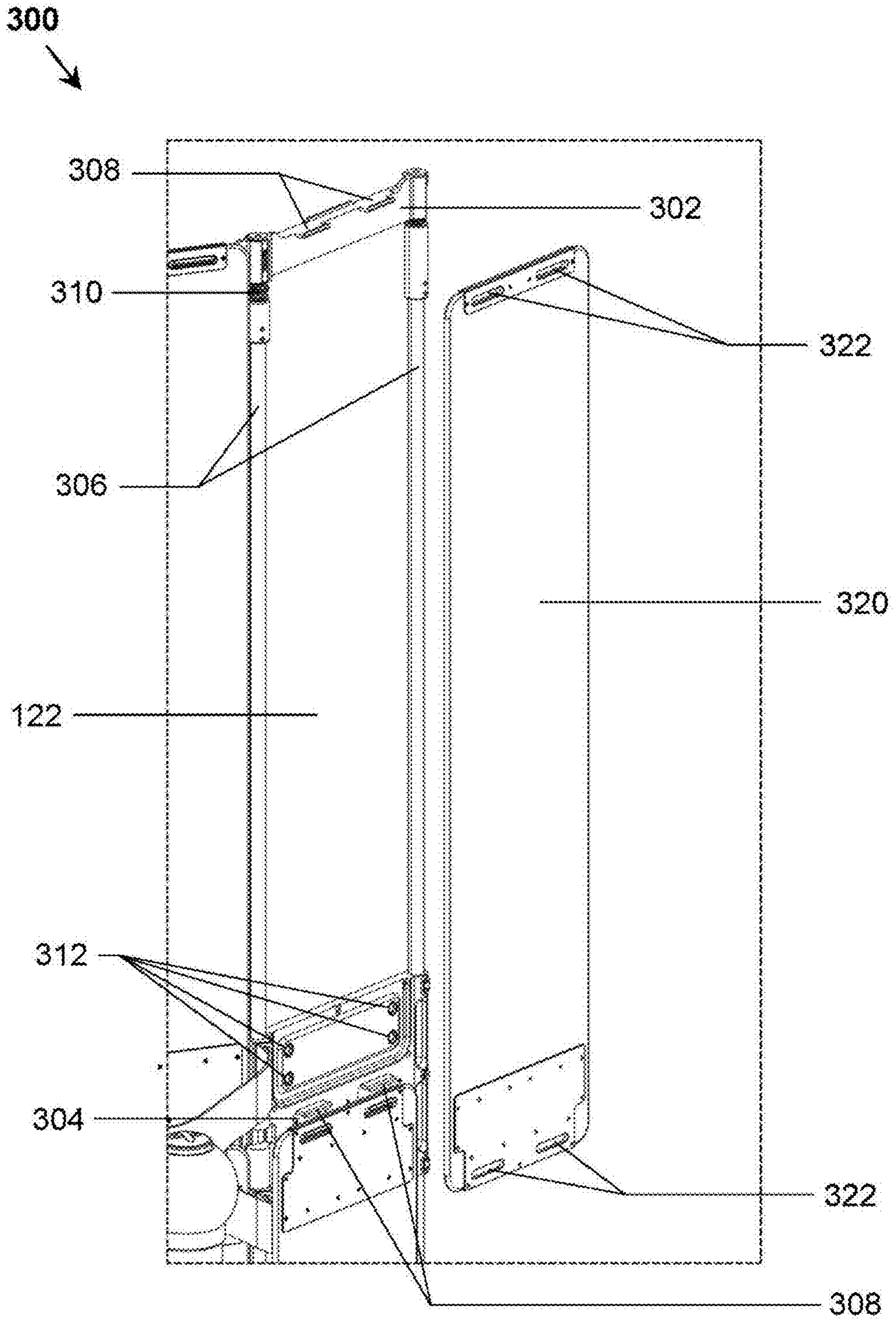
Figure 3B:
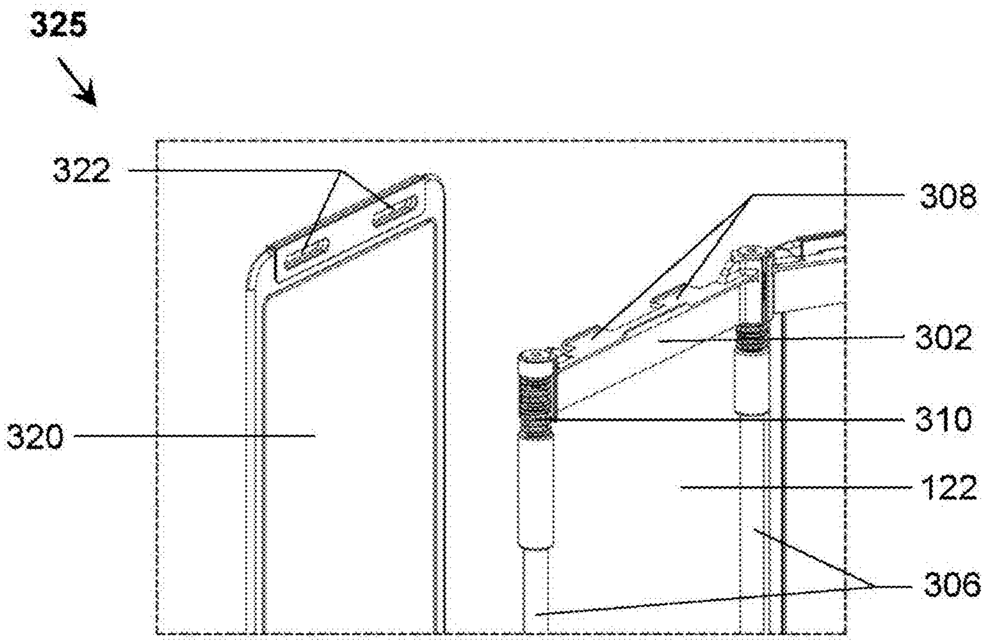
Figure 3C:
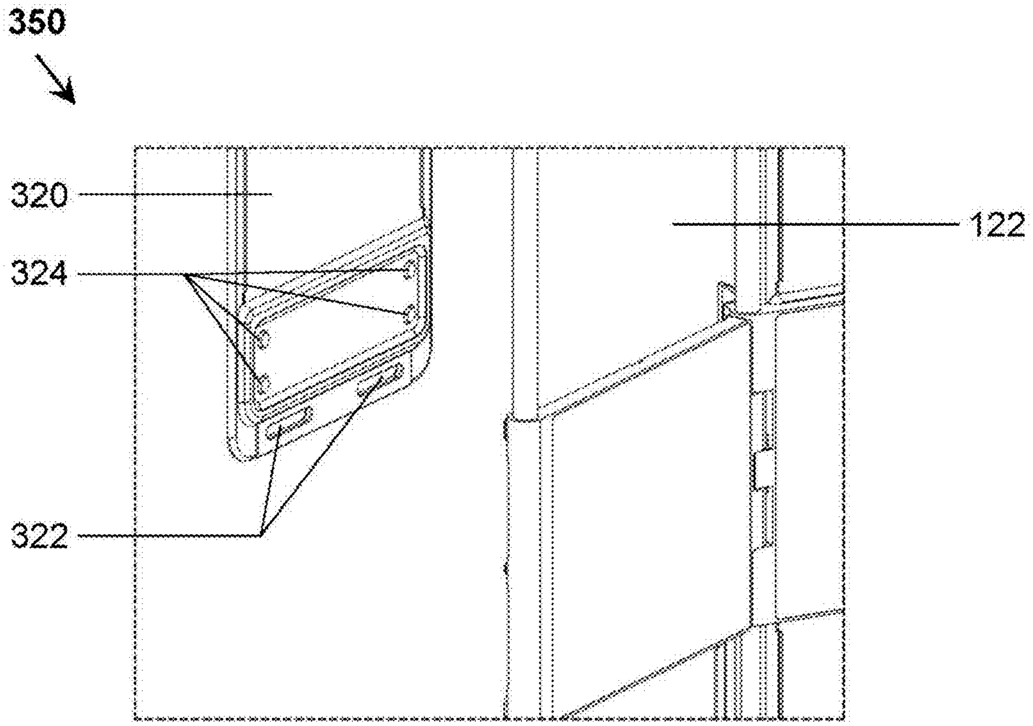
Figure 4A:
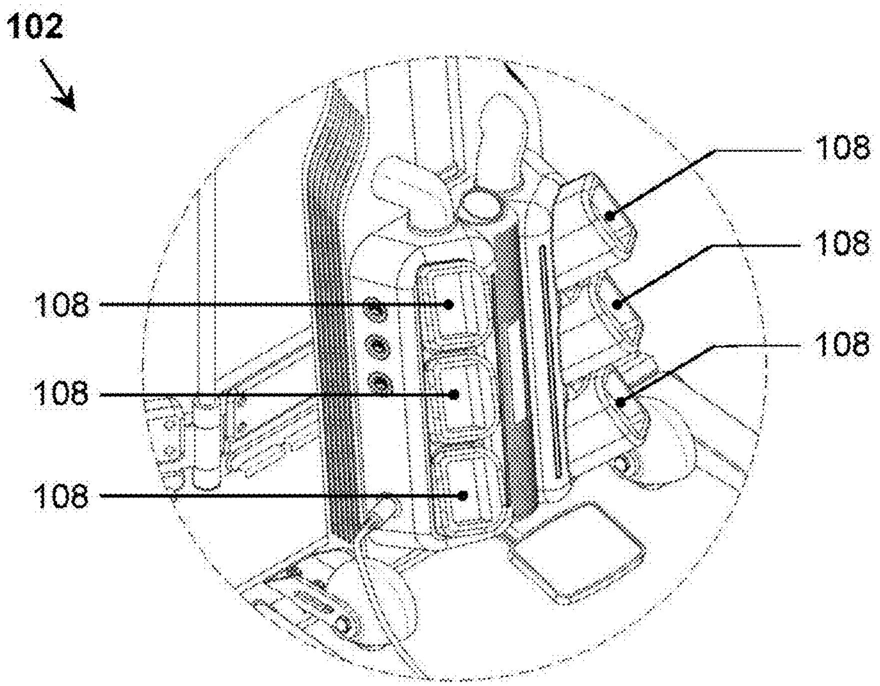
Figure 4B:
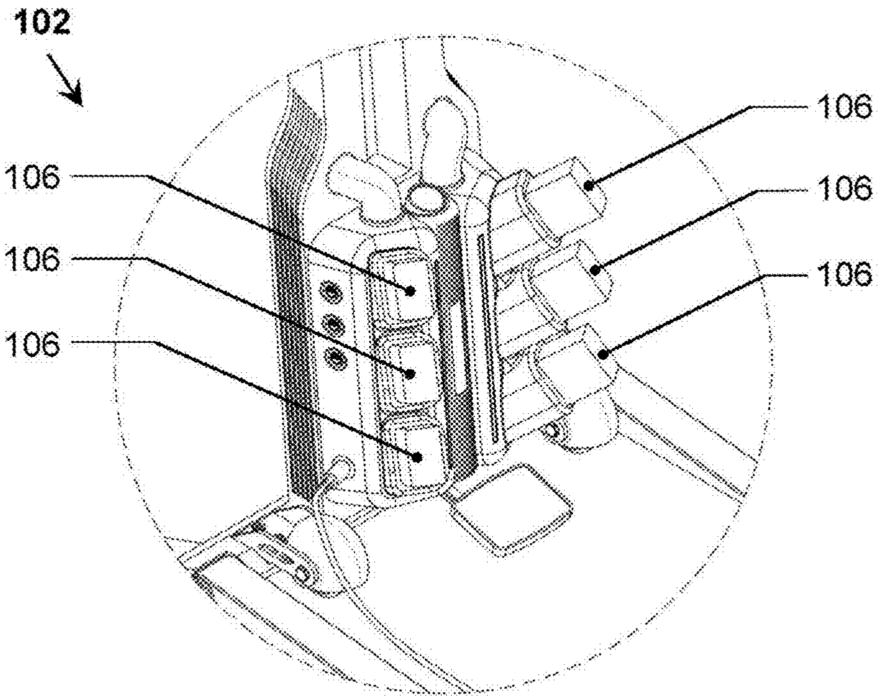
Figure 5:
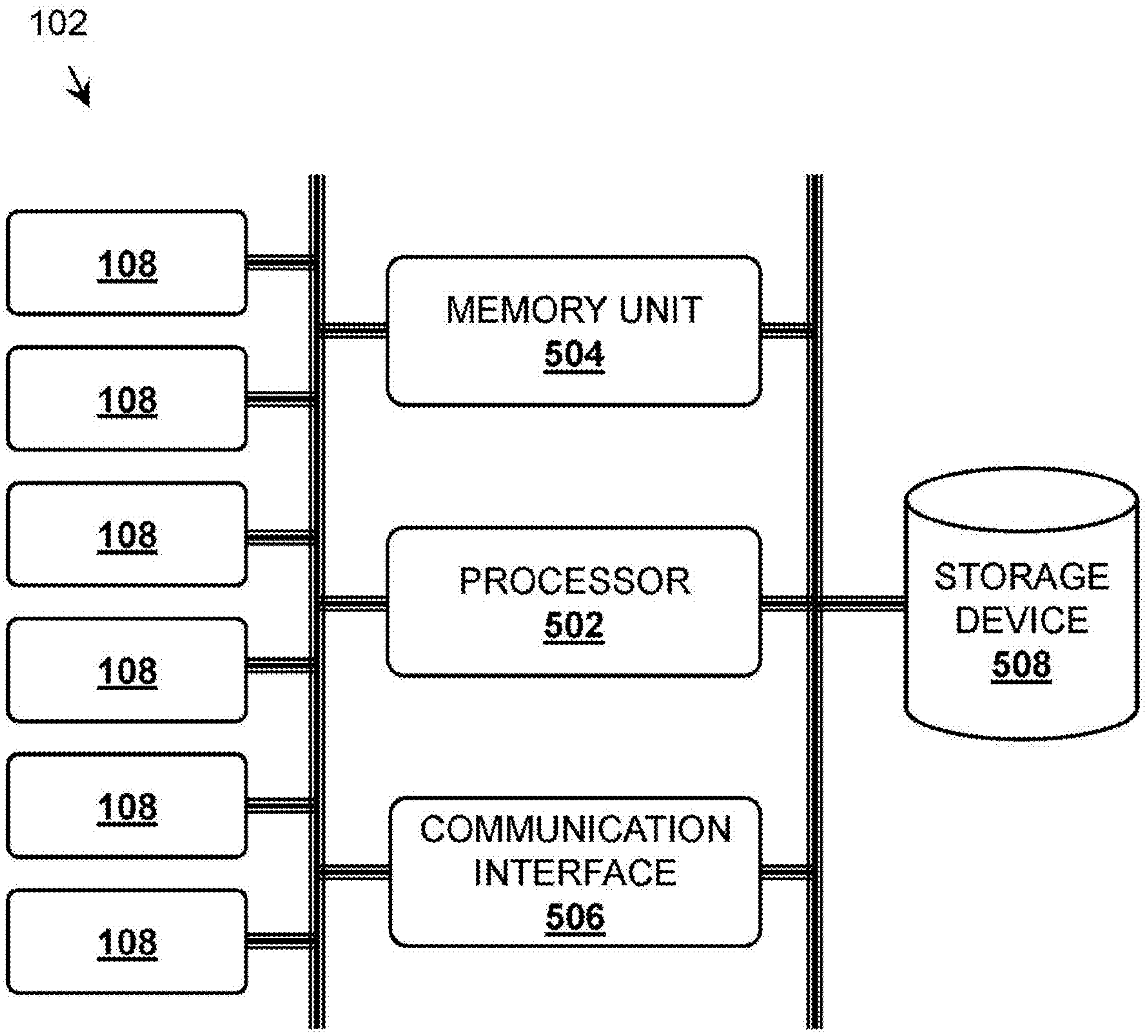
Figure 6:
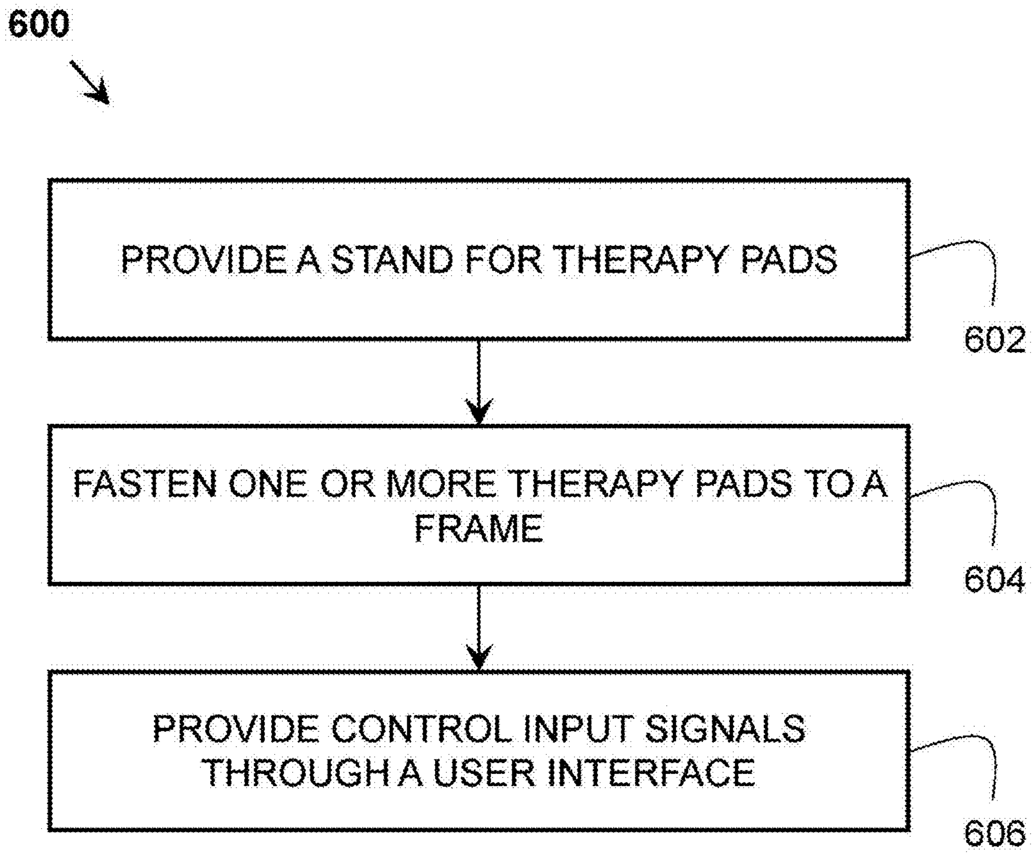
Figure 7:
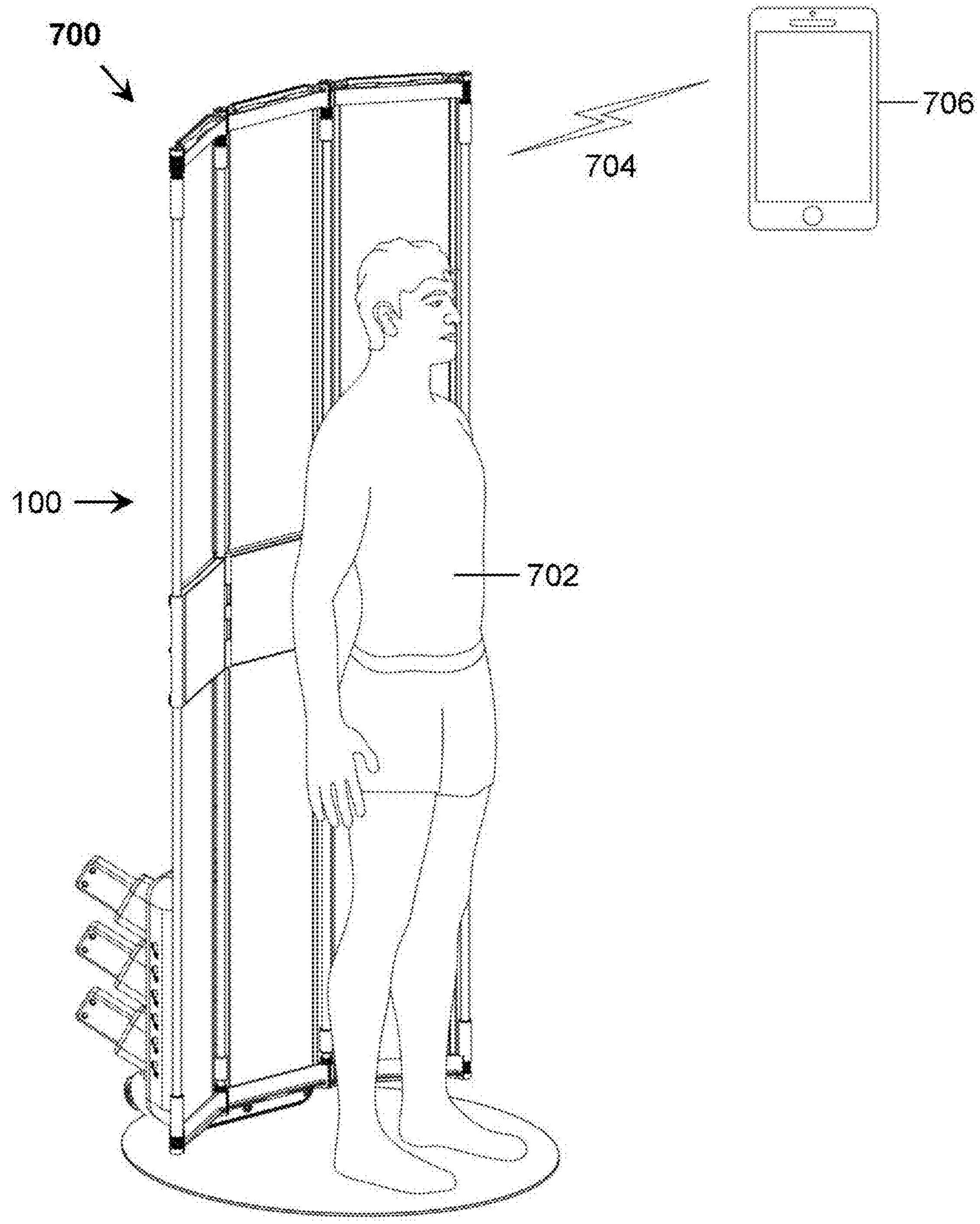

FIG. 3A a partial perspective view of a second holding panel and a therapy pad in accordance with an embodiment of the present invention;

FIG. 3B a partial perspective view of a top portion of the second holding panel and the therapy pad in accordance with an embodiment of the present invention;

FIG. 3C a partial perspective view of a bottom portion of the second holding panel and the therapy pad in accordance with an embodiment of the present invention;

FIG. 4A illustrates a perspective view of a control module of the stand, with empty docking stations, in accordance with an embodiment of the present invention;

FIG. 4B illustrates a perspective view of the control module of the stand, with several energy storage units in the respective docking stations, in accordance with an embodiment of the present invention;

FIG. 5 illustrates a logical diagram of the control module, in accordance with an embodiment of the present invention;

FIG. 6 illustrates a method of using the stand for the therapy pads, in accordance with an embodiment of the present invention; and FIG. 7 illustrates an application scenario for the stand for the therapy pads, in accordance with an embodiment of the present invention.

DETAILED DESCRIPTION

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure. The following detailed description is therefore not to be taken in a limiting sense, and the scope of the present invention disclosure is defined by the appended claims. Embodiments of the claims may, however, be embodied in many different forms and should not be construed as limited to the embodiments set forth herein.

Embodiments of the present invention provide a stand for the therapy pads. The stand includes a control module and a frame for installing several therapy pads. The control module includes several docking stations configured to receive several energy storage units capable of storing electrical energy for powering the several therapy pads. Electrical conductors running through the frame terminate at respective power supply terminals in the frame and connect the energy storage units with the respective power supply terminals. The therapy pads are envisaged to include power-receiving terminals that are mechanically and electrically coupled with respective power supply terminals to receive electrical energy from the energy storage units. The mechanical coupling between the power supply terminals of the frame and the power-receiving terminals of the therapy pads may be enabled through magnets, however, other coupling mechanisms such as plugs and sockets, surface mounting, through hole coupling are envisaged to be within the scope of the present invention.

The frame includes two telescopic members capable of expanding and retracting and pivotably coupled to each other. A first telescopic member is attached to the control module and a second telescopic member includes a holding bracket at a distal end of the second telescopic member. The first telescopic member may include a first movable arm and a first stationary arm, the first movable arm configured to translate relative to the first stationary arm. Furthermore, a translation lock may be provided between the first movable arm and the first stationary arm, the translation lock configured to arrest the translation of the first movable arm relative to the first stationary arm. The second telescopic member may include a second movable arm and a second stationary arm, the second movable arm configured to translate relative to the second stationary arm. Furthermore, an actuator arm (hydraulic, pneumatic, or electrical) may be connected between the first movable arm and the second movable arm.

Furthermore, one or more first holding panels are coupled to the holding bracket. The one or more first holding panels are configured to fasten thereupon the therapy pads. In several embodiments of the invention, the holding bracket is coupled to the distal end of the second telescopic member through a joint that allows the holding bracket to pivot with respect to the distal end of the second telescopic member in at least two degrees of freedom. The frame also includes one or more second holding panels capable of pivoting with respect to the one or more first holding panels. Furthermore, each holding panel of the one or more first holding panels and the one or more second holding panels includes a top member, a bottom member, and one or more lateral members connecting the top member and the bottom member.

In several embodiments of the invention, the respective lengths of the one or more lateral members may be adjustable to fit several different sizes of the therapy pads. Furthermore, each one of the top members and the bottom members may be provided with engaging members configured to engage with complementary engaging members of the therapy pads to fasten the therapy pads to the holding panels. Also, the power supply terminals may be provided adjacent to the top members and/or the bottom members. The frame may further be provided with one or more shoes to support the control module and the frame on level ground. Furthermore, the one or more shoes may include wheels for transporting the stand from one location to another location. During operation or usage, control input signals to modify operational characteristics of the one or more therapy pads installed with the frame may be provided to the control module through a user interface provided with the control module or through a communication interface communicating with a user computing device over a communication network.

Several embodiments of the present invention will now be discussed in detail with reference to FIGS. 1A-6.

Figure 1A:
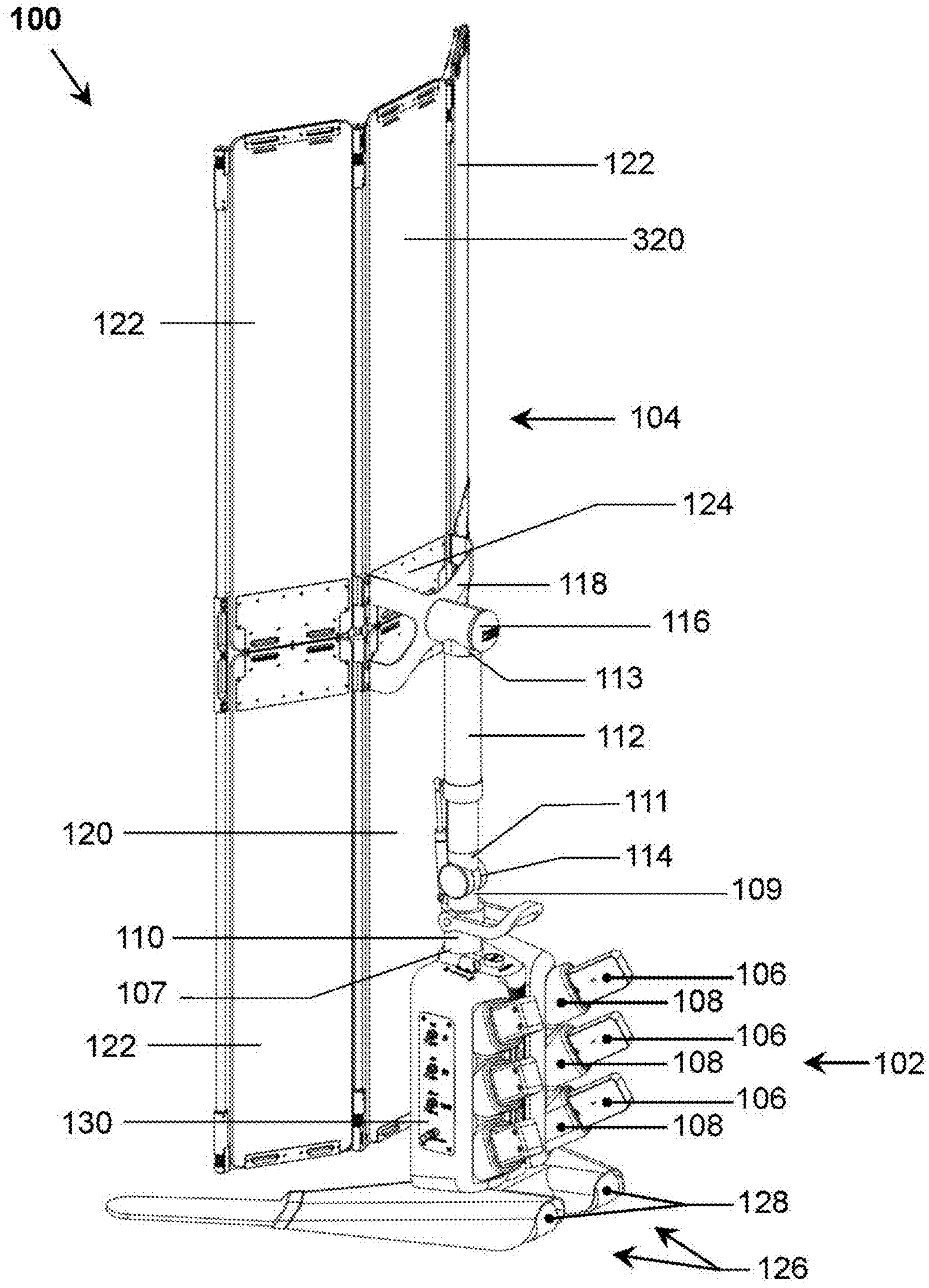
FIG. 1A illustrates a rear perspective view of a stand for therapy pads, in accordance with an embodiment of the present invention.
Figure 1B:
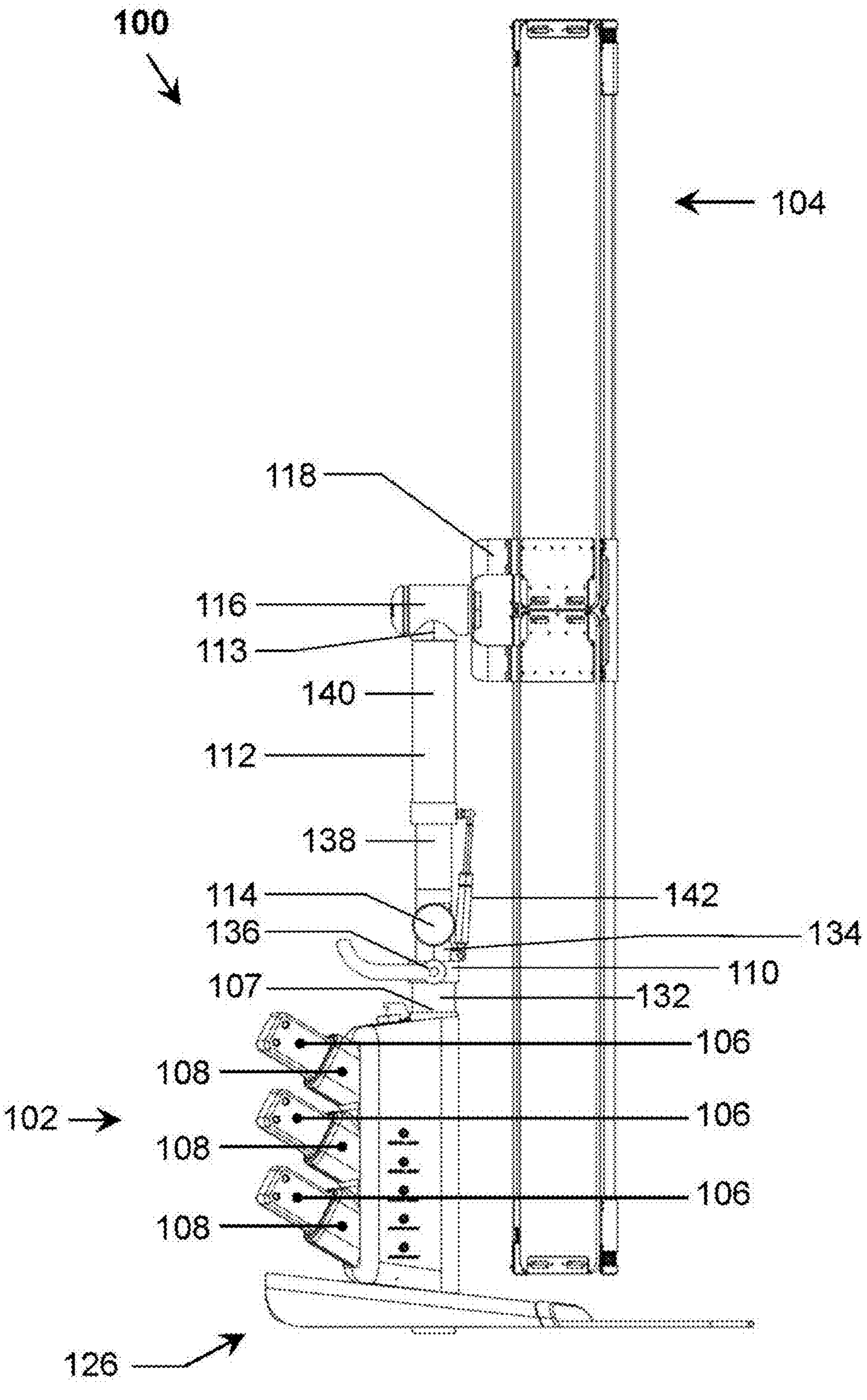
FIG. 1B illustrates a left-side view of the stand for the therapy pads, in accordance with an embodiment of the present invention.
Figure 1C:
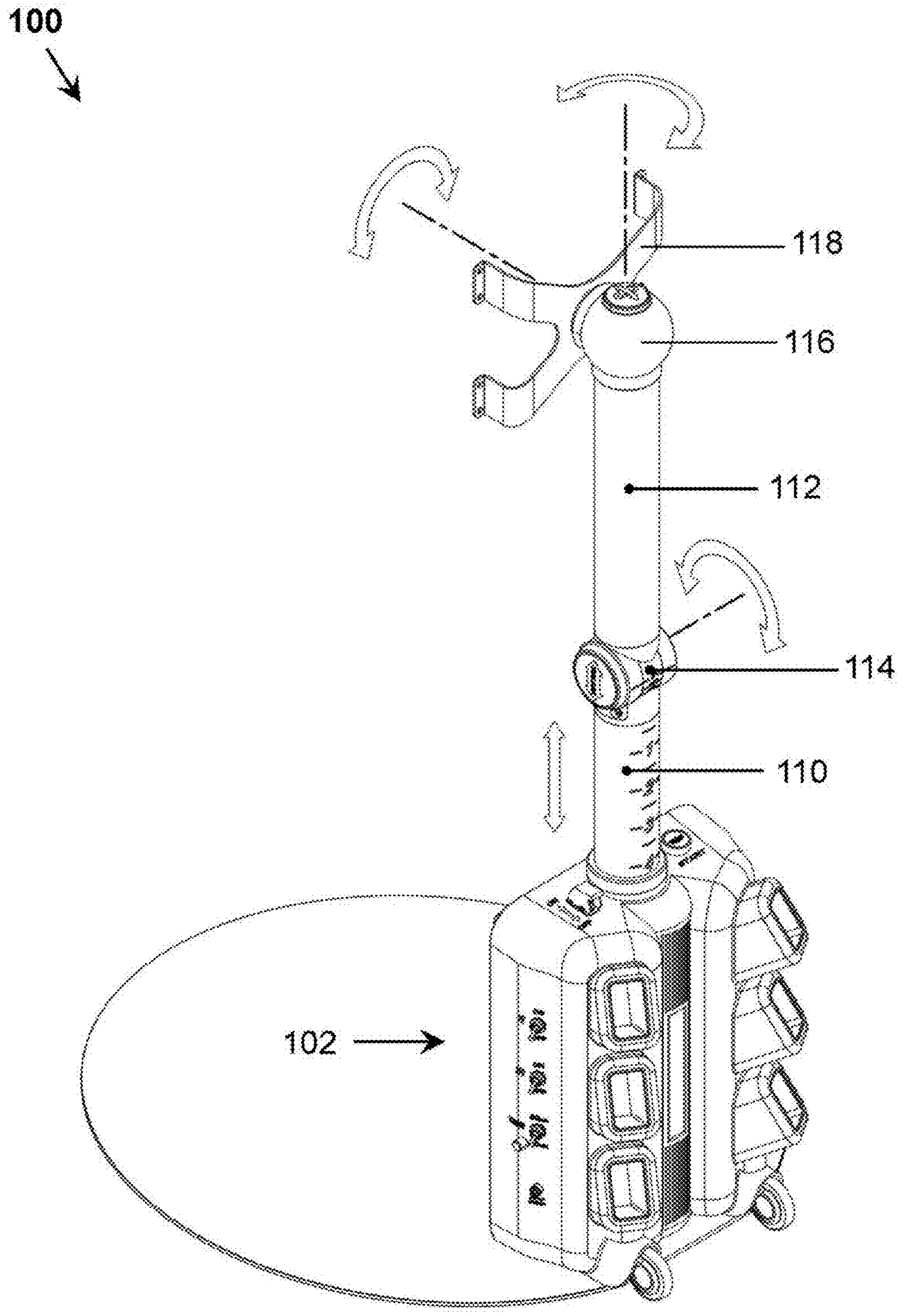
FIG. 1C illustrates a partial perspective view of the stand for the therapy pads, in accordance with an embodiment of the present invention.

FIG. 1A illustrates a rear perspective view of a stand 100 for therapy pads, in accordance with an embodiment of the present invention. FIG. 1B illustrates a left-side view of the stand 100 for the therapy pads, in accordance with an embodiment of the present invention. FIG. 1C illustrates a partial perspective view of the stand 100 for the therapy pads, in accordance with an embodiment of the present invention. It is to be noted that all the elements of the stand 100 may be made from a combination of materials selected from group consisting of thermoplastics (for example, polypropylene, nylon, thermoplastic polyurethane, etc.), thermosetting plastics (for example, phenolic resins, epoxy resins, etc.), composites (for example, carbon fiber, fiberglass), and metals (for example, steel, aluminum, etc.). Referring to FIGS. 1A, 1B, and 1C, the stand 100 includes a control module 102 and a frame 104. The control module 102 is located in proximity to a lower portion of the frame 104 and closer to the level ground.

Figure 1D:
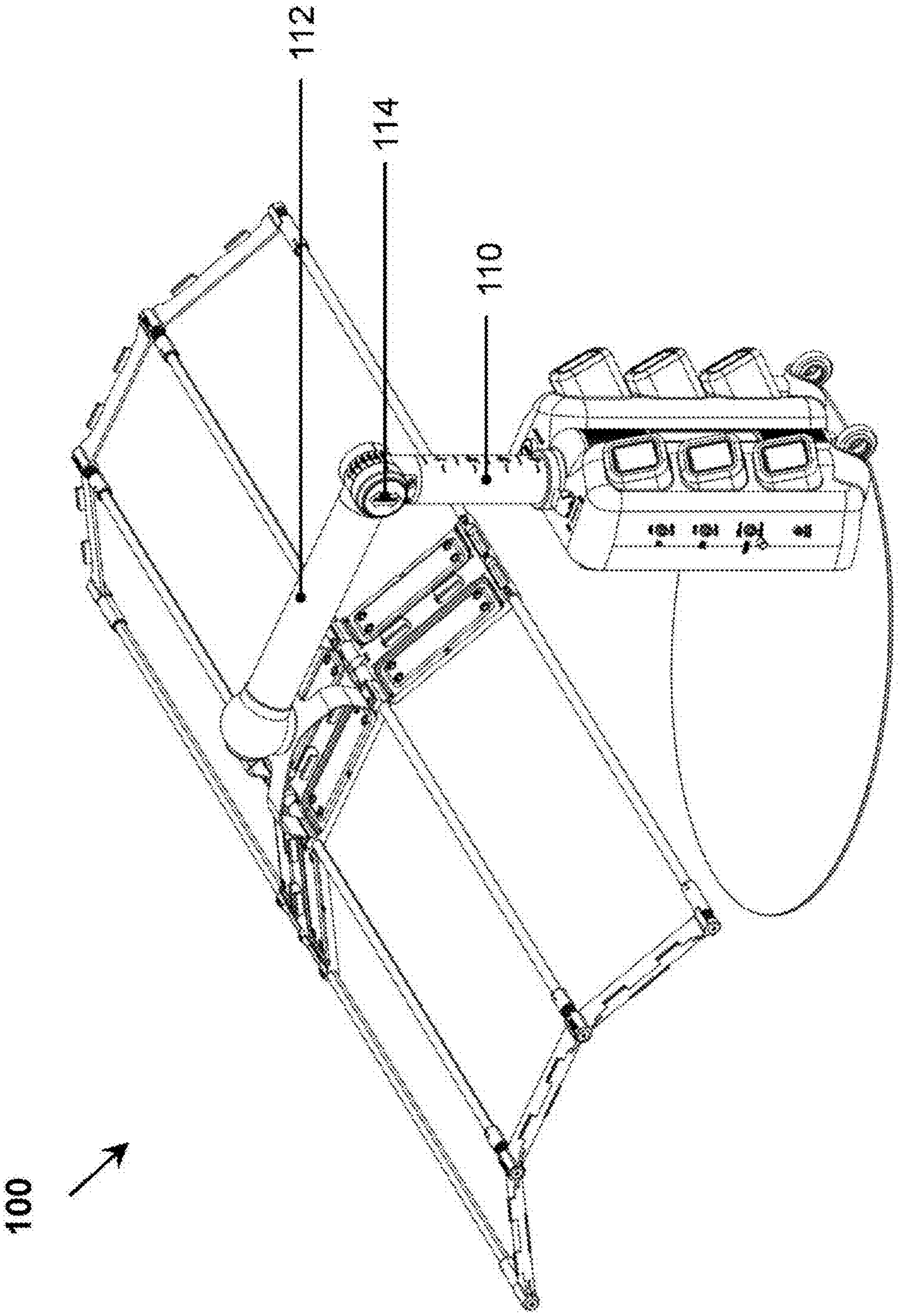
FIG. 1D illustrates a first alternative configuration of the stand for the therapy pads, in accordance with an embodiment of the present invention.

The frame 104 includes a first telescopic member 110 and a second telescopic member 112. The first telescopic member 110 includes a first proximal end 107 and a first distal end 109. Similarly, the second telescopic member 112 includes a second proximal end 111 and a second distal end 113. The first proximal end 107 is coupled to the control module 102. The first distal end 109 is pivotably coupled to the second proximal end 111 through a first pivotable joint 114. FIG. 1D illustrates a first alternative configuration of the stand 100 for the therapy pads, in accordance with an embodiment of the present invention. As illustrated in FIG.

1D, the second telescopic member 112 is pivoted with respect to the first telescopic member 110 through the first pivotable joint 114.

Referring to FIGS. 1A and 1B, a first length of the first telescopic member 110 is adjustable. In that regard, the first telescopic member 110 includes a first stationary arm 132 and a first movable arm 134. The first movable arm 134 is configured to translate relative to the first stationary arm 132. A translation lock 136 has been provided between the first movable arm 134 and the first stationary arm 132. The translation lock 136 is configured to arrest the translation of the first movable arm 134 relative to the first stationary arm 132. Similarly, a second length of the second telescopic member 112 is adjustable too. In that regard, the second telescopic member 112 includes a second movable arm 140 and a second stationary arm 138. The second movable arm 140 is configured to translate relative to the second stationary arm 138. An actuator arm 142 is connected between the first movable arm 134 and the second movable arm 140. The actuator arm 142 is configured to cause extension of the second telescopic members 112. Further, the first telescopic member 110 and the second telescopic members 112 may be powered through an electrical motor, a hydraulic motor, pneumatic motor, and combinations thereof.

Figure 1E:
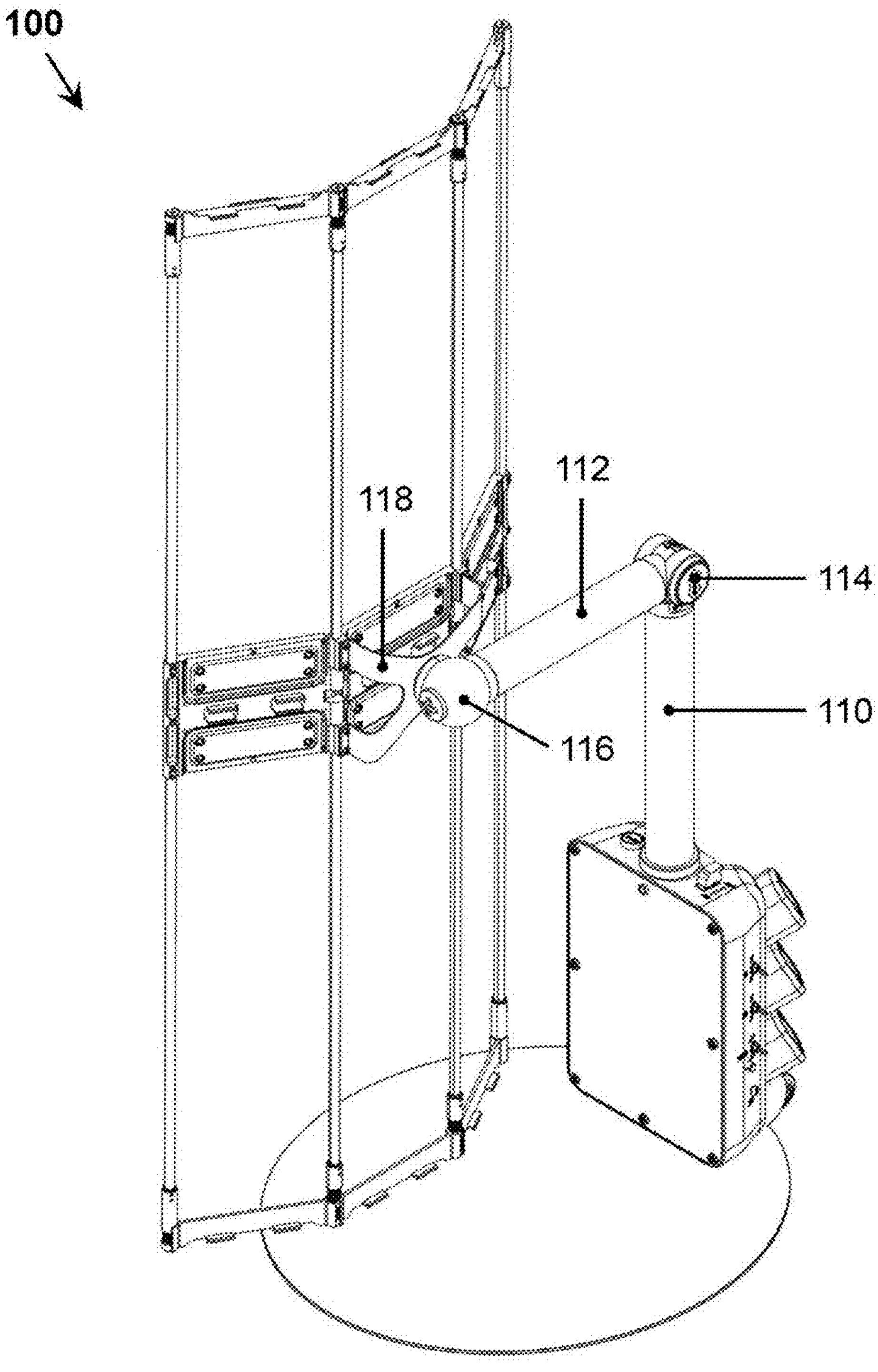
FIG. 1E illustrates a second alternative configuration of the stand for the therapy pads, in accordance with an embodiment of the present invention.

A holding bracket 118 is pivotably coupled to the second distal end 113 through a second pivotable joint 116. In several embodiments of the invention, the second pivotable joint 116 allows rotation of the holding bracket 118 in one degree of freedom, as depicted in FIGS. 1A and 1B. In several alternate embodiments of the invention, the second pivotable joint 116 allows rotation of the holding bracket 118 in at least two degrees of freedom, as depicted in FIG. 1C. FIG. 1E illustrates a second alternative configuration of the stand 100 for the therapy pads, in accordance with an embodiment of the present invention. As illustrated in FIG. 1E, the holding bracket 118 is pivoted with respect to the second telescopic member 112 through the second pivotable joint 116. Referring to FIGS. 1A and 1B, one or more first holding panels 120 are fastened to the holding bracket 118.

Figure 2A:
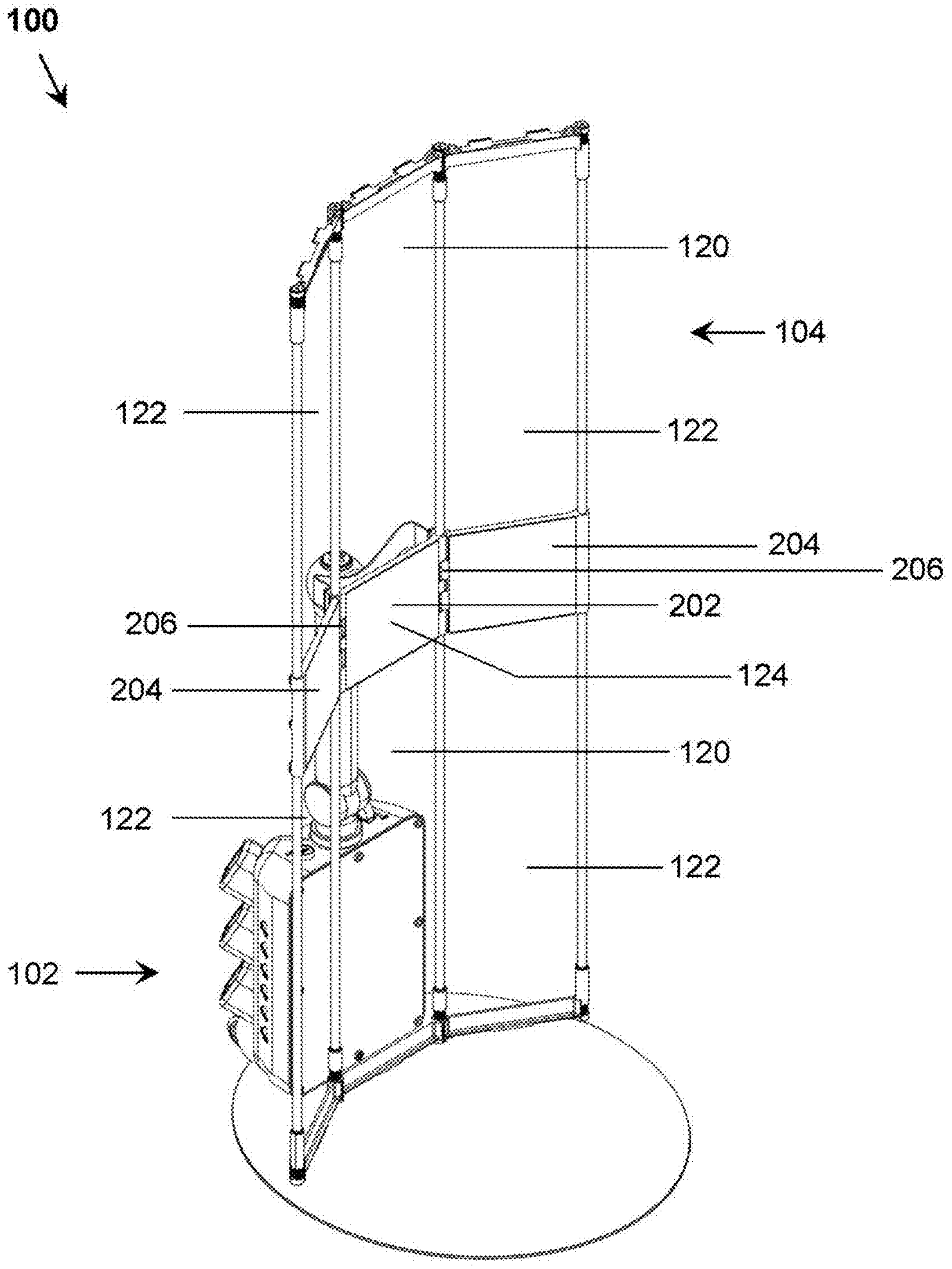
FIG. 2A illustrates a front perspective view of the stand for the therapy pads, in accordance with an embodiment of the present invention.

FIG. 2A illustrates a front perspective view of the stand 100 for the therapy pads, in accordance with an embodiment of the present invention. The one or more first holding panels 120 are fastened to the holding bracket 118 through a panel fastening bracket 124. The panel fastening bracket 124 includes a first panel fastening segment 202 and one or more second panel fastening segments 204. The one or more second panel fastening segments 204 are pivotably coupled to the first panel fastening segment 202 through one or more respective hinge joints 206. The one or more second panel fastening segments 204 are configured to fasten thereto one or more second holding panels 122, thereby allowing the one or more second holding panels 122 to be pivotably coupled to the one or more first holding panels 120. The one or more second holding panels 122 are also configured to fasten thereupon the one or more respective therapy pads.

Figure 2B:
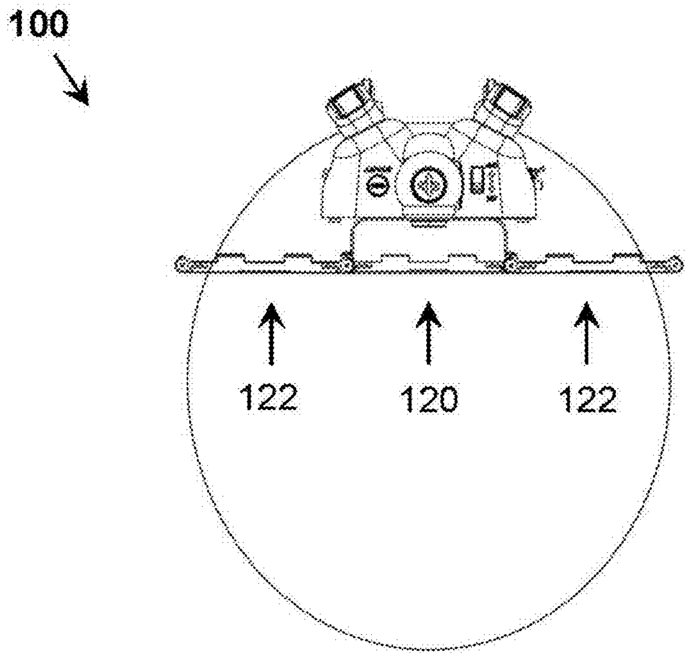
FIG. 2B illustrates a top view of the stand for therapy pads, in a first configuration, in accordance with an embodiment of the present invention.
Figure 2C:
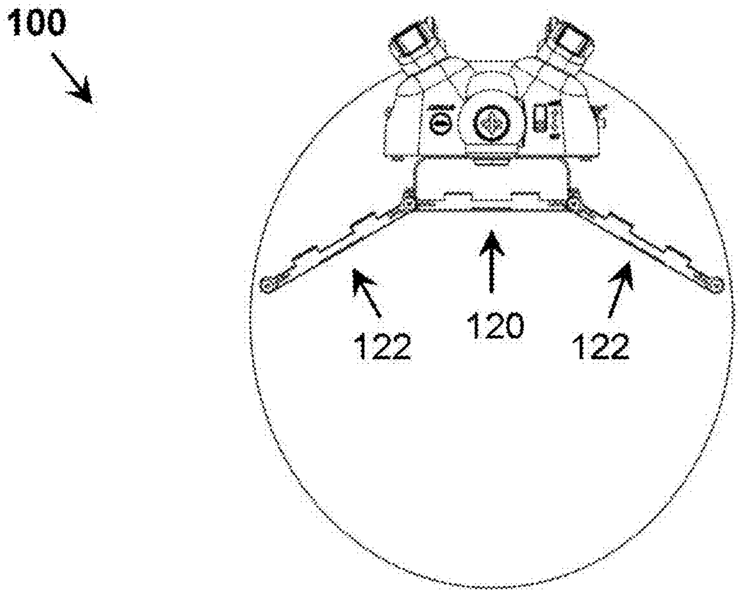
FIG. 2C illustrates a top view of the stand for therapy pads, in a second configuration, in accordance with an embodiment of the present invention.

FIG. 2B illustrates a top view of the stand 100 for therapy pads, in a first configuration, in accordance with an embodiment of the present invention. In the first configuration, the one or more first holding panels 120 are in line with the one or more second holding panels 122. FIG. 2C illustrates a top view of the stand 100 for therapy pads, in a second configuration, in accordance with an embodiment of the present invention. In the second configuration, the one or more second holding panels 122 are pivoted with respect to the one or more first holding panels 120. The one or more first holding panels 120 and the one or more second holding panels 122 are envisaged to include identical constructional features as will be discussed in the following discussion.

FIG. 3A a partial perspective view 300 of a second holding panel 122 and a therapy pad 320 in accordance with an embodiment of the present invention. The second holding panel 122 includes a top member 302, a bottom member 304, and one or more lateral members 306 connecting the top member 302 and the bottom member 304. Although the one or more lateral members 306 have been illustrated as parallel bars, they may also take the shape of slabs or panels without departing from the scope of the invention. Furthermore, the one or more lateral members 306 include height adjustment mechanisms 310 such as threads, slots and pins, telescopic arms, etc. to enable respective lateral lengths of the one or more lateral members 306 to be adjustable for accommodating therapy pads of varying sizes.

Furthermore, each one of the top member 302 and the bottom member 304 includes one or more engaging members 308 configured to engage with complementary engaging members 322 of the therapy pad 320. The engaging members 308 have been depicted in the form of protrusions and the complementary engaging members 322 of the therapy pad 320 have been depicted as slots for accommodating the protrusions. However, other engaging arrangements such as loop and hook fasteners, snap-fits arrangements, adhesive bonding, clips, magnetic fastening, threaded fasteners, rivets, and pins are envisaged to be within the scope of the invention. The second holding panel 122 and by extension, the first holding panel 120 also includes one or more power supply terminals 312 to supply electrical power to the therapy pad 320.

FIG. 3B a partial perspective view 325 of a top portion of the second holding panel 122 and the therapy pad 320 in accordance with an embodiment of the present invention. FIG. 3C a partial perspective view 350 of a bottom portion of the second holding panel 122 and the therapy pad 320 in accordance with an embodiment of the present invention. The therapy pad 320 includes one or more power-receiving terminals 324 configured to receive electrical power from the one or more power supply terminals 312. In several embodiments of the invention, the one or more power supply terminals 312 are configured to mechanically couple to the one or more respective power-receiving terminals 324 through magnetic coupling.

Referring to FIGS. 1A and 1B, the control module 102 includes a plurality of docking stations 108 configured to receive a plurality of respective energy storage units 106. The control module 102 is configured to supply electrical power to the one or more therapy pads through the one or more power supply terminals 312 included within the frame 104. Further, the stand 100 includes one or more shoes 126 configured to support the control module 102 and the frame 104. Furthermore, each one of the one or more shoes 126 includes a wheel 128 for transporting the stand 100 from one location to another location. In several embodiments of the invention, the control module 102 further includes a user interface 130 configured to receive control input signals to modify operational characteristics of the one or more therapy pads. The user interface 130 may be embodied as a single toggle, a group of toggles, a touchpad, and combinations thereof. FIG. 4A illustrates a perspective view of the control module 102, with empty docking stations 108, in accordance with an embodiment of the present invention. FIG. 4B illustrates a perspective view of the control module 102, with several energy storage units 106 in the respective docking stations 108, in accordance with an embodiment of the present invention. In several embodiments of the invention, the energy storage units 106 may be rechargeable batteries such as Lithium-ion batteries, Lithium-polymer batteries, and Nickel-Metal-Hydride batteries.

FIG. 5 illustrates a logical diagram of the control module 102, in accordance with an embodiment of the present invention. The control module 102 includes docking stations 108, a processor 502, a memory unit 504, a communication interface 506, and a storage device 508. The memory unit 504 may include machine-readable instructions at run time that when executed by the processor 502 would allow the control module 102 to perform several automated or electronically controlled functions during the operation and/or the utilization of the stand 100.

FIG. 6 illustrates a method 600 of using the stand 100 for the therapy pads, in accordance with an embodiment of the present invention. The method begins at Step 602, when the stand 100 as described in several embodiments in the preceding discussion is provided. At Step 602, the one or more therapy pads are fastened to the frame 104, as a result wherein, the one or more complementary power-receiving terminals 324 of the one or more respective therapy pads make contact with the one or more respective power supply terminals 312 of the frame 104. The therapy pads may be configured to provide several forms of therapies such as irradiation, vibratory massage, electrode therapy, ultrasonic wave therapy, heating, cooling, and combinations thereof. At Step 606, the control input signals are provided through the user interface 130 to modify the operational characteristics of the one or more therapy pads.

FIG. 7 illustrates an application scenario 700 for the stand 100 for the therapy pads, in accordance with an embodiment of the present invention. As illustrated in FIG. 7, a user 702 receives the therapy using the stand 100 and provides the control input signals from a user computing device 706 (such as a smartphone, a tablet PC, a notebook PC, a desktop PC, and the like) through the communication interface 506 of the control module 102 over a communication network 704. In several embodiments of the invention, the first and the second lengths of the first 110 and the second 112 telescopic members respectively are adjusted. In several embodiments of the invention, the adjusting of the first and the second lengths of the first 110 and the second 112 telescopic members respectively is performed through the control module 102. In several embodiments of the invention, the translation of the first movable arm 134 relative to the first stationary arm 132 is arrested by engaging the translation lock 136. In several embodiments of the invention, the arresting of the translation of the first movable arm 134 relative to the first stationary arm 132 by engaging the translation lock 136 is performed through the control module 102. Furthermore, in several embodiments of the invention, the stand 100 is transported from one location to another location using the wheels 128.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to provide the broadest scope consistent with the principles and the novel and inventive features disclosed or suggested herein. Accordingly, the invention is anticipated to hold on to all other such alternatives, modifications, and variations that fall within the scope of the present invention and appended claims.

The invention claimed is:

1. A stand for therapy pads, the stand comprising:

a control module comprising a plurality of docking stations configured to dock therewithin a plurality of respective energy storage units, the plurality of energy storage units configured to store electrical energy; and a frame mechanically coupled to the control module, the frame comprising one or more first holding panels and one or more second holding panels pivotably coupled to the one or more first holding panels, wherein each of the one or more first holding panels and the one or more second holding panels is configured to detachably support a respective therapy pad from a plurality of therapy pads, wherein each of the one or more first holding panels and the one or more second holding panels includes one or more power supply terminals, wherein the control module is configured to supply electrical power to the plurality of therapy pads through one or more power supply terminals disposed on the one or more first holding panels and the one or more second holding panels, the one or more power supply terminals configured to contact one or more complementary power-receiving terminals of the plurality of therapy pads, and wherein the plurality of therapy pads, while detachably mounted to the one or more first holding panels and the one or more second holding panels, receive operating power from the plurality of energy storage units through the one or more power supply terminals, and are simultaneously powered and operated in a coordinated manner to deliver therapy to multiple body parts of a user.

2. The stand as claimed in claim 1, wherein the one or more power supply terminals are configured to mechanically couple to the one or more respective power-receiving terminals through magnetic coupling.

3. The stand as claimed in claim 1, wherein the frame further comprises:

a first telescopic member comprising a first proximal end and a first distal end, the first proximal end fastened to the control module, wherein a first length of the first telescopic member is adjustable, a second telescopic member comprising a second proximal end and a second distal end, the second proximal end pivotably coupled to the first distal end, wherein a second length of the second telescopic member is adjustable, a holding bracket pivotably coupled to the second distal end, wherein the holding bracket is configured to pivot about the second distal end, the one or more first holding panels fastened to the holding bracket, the one or more first holding panels configured to fasten thereupon the one or more respective therapy pads, and the one or more second holding panels configured to fasten thereupon one or more respective therapy pads.

4. The stand as claimed in claim 3, wherein each one of the one or more first holding panels and the one or more second holding panels comprises a top member, a bottom member, and one or more lateral members connecting the top member and the bottom member, wherein the top member, the bottom member, and the one or more lateral members altogether define a receiving region configured to receive at least a portion of a respective therapy pad between the top member and the bottom member.

5. The stand as claimed in claim 4, wherein each one of the top member and the bottom member comprises one or more engaging members configured to removably retain the therapy pad within the receiving region by engaging complementary engaging members of the therapy pads.

6. The stand as claimed in claim 4, wherein one or more respective lateral lengths of the one or more lateral members are adjustable.

7. The stand as claimed in claim 3, wherein the first telescopic member comprises a first movable arm and a first stationary arm, the first movable arm configured to translate relative to the first stationary arm, the second telescopic member comprises a second movable arm and a second stationary arm, the second movable arm configured to translate relative to the second stationary arm, the frame further comprising an actuator arm connected between the first movable arm and the second movable arm.

8. The stand as claimed in claim 7, further comprising a translation lock provided between the first movable arm and the first stationary arm, the translation lock configured to arrest the translation of the first movable arm relative to the first stationary arm.

9. The stand as claimed in claim 1, further comprising one or more shoes configured to support the control module and the frame.

10. The stand as claimed in claim 9, wherein each one of the one or more shoes comprises a wheel for transporting the stand from one location to another location.

11. The stand as claimed in claim 1, wherein the control module further comprises a user interface configured to receive control input signals to modify operational characteristics of the one or more therapy pads.

12. The stand as claimed in claim 1, wherein the control module further comprises a communication interface configured to receive control input signals from a user computing device, over a communication network, to modify operational characteristics of the one or more therapy pads.

13. A stand for therapy pads, the stand comprising:
- a control module comprising a plurality of docking stations configured to receive a plurality of removable energy storage units, each removable energy storage unit configured to store electrical energy;
- a frame mechanically coupled to the control module, the frame comprising:
  - one or more first holding panels; and
  - one or more second holding panels pivotably coupled to the one or more first holding panels,
- wherein each of the one or more first holding panels and the one or more second holding panels comprises a support structure including:
  - a top member:
  - a bottom member spaced apart from the top member; and
  - one or more lateral members extending between the top member and the bottom member,
- wherein the top member, the bottom member, and the one or more lateral members altogether define a receiving region configured to removably receive at least a portion of a respective therapy pad therebetween,
- wherein each support structure comprises one or more engaging members configured to removably retain the respective therapy pad within the receiving region by engaging complementary engaging members of the respective therapy pad,
- wherein the one or more first holding panels and the one or more second holding panels are arranged around a treatment region such that, when a plurality of therapy pads are mounted thereon, the plurality of therapy pads at least partially surround the treatment region and direct therapeutic light toward the treatment region from a plurality of different directions simultaneously,
- wherein each of the one or more first holding panels and the one or more second holding panels further comprises one or more power supply terminals disposed within the respective support structure,
- wherein each therapy pad comprises one or more complementary power-receiving terminals configured to magnetically couple to and electrically contact a respective one of the one or more power supply terminals when the therapy pad is removably retained within the receiving region,
- wherein the plurality of docking stations and the plurality of removable energy storage units are disposed within the control module at a location spaced apart from the one or more power supply terminals disposed within the one or more first holding panels and the one or more second holding panels, and
- wherein the control module is configured to simultaneously supply electrical power from two or more of the removable energy storage units to two or more of the therapy pads through different respective power supply terminals while the two or more therapy pads are mounted on different holding panels surrounding the treatment region.

14. The stand as claimed in claim 13, wherein at least one of the one or more second holding panels is pivotable relative to the one or more first holding panels to vary an angular orientation of a corresponding therapy pad with respect to the treatment region.

15. The stand as claimed in claim 13, wherein the frame is selectively configurable between:
- a first configuration in which the one or more first holding panels and the one or more second holding panels are positioned above the treatment region such that the plurality of therapy pads direct therapeutic light downward toward the treatment region; and
- a second configuration in which at least one of the one or more second holding panels is pivoted relative to the one or more first holding panels such that the plurality of therapy pads are arranged substantially parallel to the treatment region and direct therapeutic light laterally toward the treatment region.

16. A method of using a stand for therapy pads, the method comprising:
- providing the stand, the stand comprising:
  - a control module comprising a plurality of docking stations configured to dock therewithin a plurality of respective energy storage units, the plurality of energy storage units configured to store electrical energy, and
  - a frame mechanically coupled to the control module, the frame comprising one or more first holding panels and one or more second holding panels pivotably coupled to the one or more first holding panels,
  - wherein each of the one or more first holding panels and the one or more second holding panels is configured to detachably support a respective therapy pad from a plurality of therapy pads,
  - wherein each of the one or more first holding panels and the one or more second holding panels includes one or more power supply terminals,
  - wherein the control module is configured to supply electrical power to the plurality of therapy pads through one or more power supply terminals disposed on the one or more first holding panels and the one or more second holding panels, the one or more power supply terminals configured to contact one or more complementary power-receiving terminals of the plurality of therapy pads, wherein the control module further comprises a user interface configured to receive control input signals to modify operational characteristics of the plurality of therapy pads;

fastening the plurality of therapy pads to the frame, as a result wherein, the one or more complementary power-receiving terminals of the one or more respective therapy pads make contact with the one or more respective power supply terminals of the frame, wherein the plurality of therapy pads receive operating power from the plurality of energy storage units through the one or more power supply terminals, and are simultaneously powered and operated in a coordinated manner to deliver therapy to a user;

providing control input signals through the user interface to modify the operational characteristics of the one or more therapy pads.

17. The method as claimed in claim 16, further comprising receiving the control input signals from a user computing device, over a communication network, to modify the operational characteristics of the one or more therapy pads.

18. The method as claimed in claim 16, wherein the frame further comprises:

a first telescopic member comprising a first proximal end and a first distal end, the first proximal end fastened to the control module, wherein a first length of the first telescopic member is adjustable, a second telescopic member comprising a second proximal end and a second distal end, the second proximal end pivotably coupled to the first distal end, wherein a second length of the second telescopic member is adjustable, wherein the first telescopic member comprises a first movable arm and a first stationary arm, the first movable arm configured to translate relative to the first stationary arm, the second telescopic member comprises a second movable arm and a second stationary arm, the second movable arm configured to translate relative to the second stationary arm, the frame further comprising an actuator arm connected between the first movable arm and the second movable arm, a holding bracket pivotably coupled to the second distal end, wherein the holding bracket is configured to pivot about the second distal end, the one or more first holding panels fastened to the holding bracket, the one or more first holding panels configured to fasten thereupon the one or more respective therapy pads, and the method further comprises adjusting the first and the second lengths of the first and the second telescopic members respectively.

19. The method as claimed in claim 18, wherein the adjusting of the first and the second lengths of the first and the second telescopic members respectively is performed through the control module.

20. The method as claimed in claim 18, wherein the stand further comprises:

a translation lock provided between the first movable arm and the first stationary arm, the translation lock configured to arrest the translation of the first movable arm relative to the first stationary arm, and the method further comprises arresting the translation of the first movable arm relative to the first stationary arm by engaging the translation lock.

21. The method as claimed in claim 20, wherein the arresting of the translation of the first movable arm relative to the first stationary arm by engaging the translation lock is performed through the control module.

22. The method as claimed in claim 16, wherein the stand further comprises:

one or more shoes configured to support the control module and the frame wherein each one of the one or more shoes comprises a wheel for transporting the stand from one location to another location, and the method further comprises transporting the stand from one location to another location.

* * * * *